United States Patent [19]
Rothschild et al.

[11] Patent Number: 5,152,800
[45] Date of Patent: Oct. 6, 1992

[54] BELOW-THE-KNEE PROSTHESIS AND METHOD OF MAKING THE SAME

[75] Inventors: Vernon R. Rothschild, St. Claire; John R. Fox, Trappe, both of Md.

[73] Assignee: Rothschild's Orthopedic Appliances, Inc., Forestville, Md.

[21] Appl. No.: 766,285

[22] Filed: Sep. 27, 1991

Related U.S. Application Data

[62] Division of Ser. No. 493,454, Mar. 14, 1990.

[51] Int. Cl.⁵ ................................................. A61F 2/78
[52] U.S. Cl. .................................................... 623/33
[58] Field of Search .................. 623/28, 29, 33, 53, 623/36, 38, 901

[56] References Cited

U.S. PATENT DOCUMENTS

| | | |
|---|---|---|
| 706,498 | 8/1902 | Seeley . |
| 795,734 | 7/1905 | Seeley . |
| 1,436,875 | 11/1922 | Greening . |
| 1,884,588 | 10/1932 | Davies . |
| 3,909,855 | 10/1975 | Barredo . |
| 4,307,056 | 12/1981 | Meyer . |
| 4,473,421 | 9/1984 | Gustafsson . |
| 4,735,754 | 4/1988 | Buckner . |
| 5,004,477 | 4/1991 | Palfray ........................... 623/33 |

FOREIGN PATENT DOCUMENTS 0038908  8/1889  United Kingdom ................. 623/53

Primary Examiner—David Isabella
Assistant Examiner—Gina M. Gualtieri
Attorney, Agent, or Firm—Sixbey, Friedman, Leedom & Ferguson

[57] ABSTRACT

A prosthesis for fitting a below-the-knee amputee is disclosed and includes a socket for receiving the stump of the below-the-knee amputee, a keel having a peripheral groove formed about the periphery of a bottom portion of the keel, a tubular shin member extending from the socket and surrounding lateral and medial portions of the keel and filling the peripheral grooves formed about the bottom portion of the keel leaving a substantial portion of the bottom of the keel exposed. A resilient foot member is then secured to the exposed portion of the keel with the material of the tubular shin member being formed into the grooves of the keel and maintaining such keel within the shin member. Also the method of manufacturing such prosthesis.

9 Claims, 2 Drawing Sheets

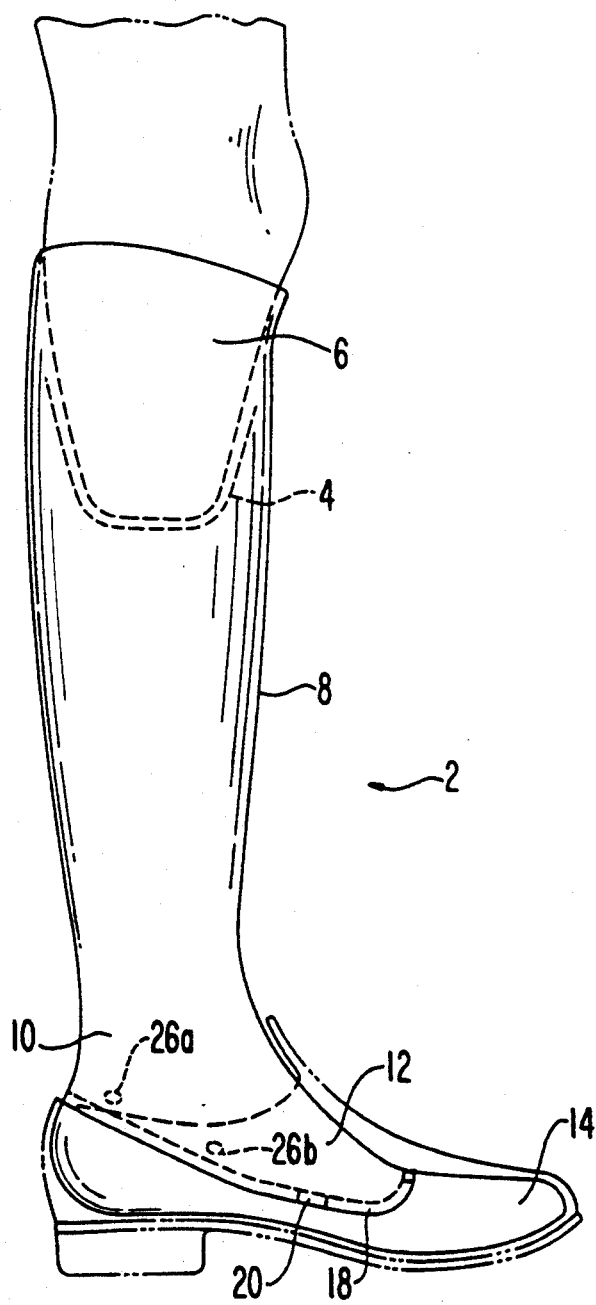
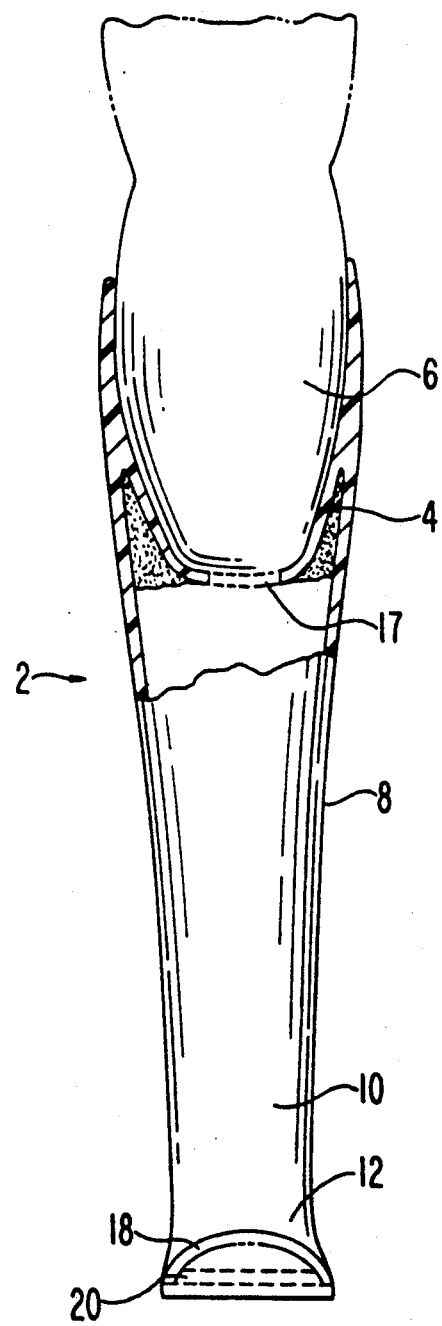

BELOW-THE-KNEE PROSTHESIS AND METHOD OF MAKING THE SAME

This is a divisional application of Ser. No. 493,454, filed Mar. 14, 1990.

TECHNICAL FIELD

This invention relates to a below-the-knee prosthesis and method of making the same. More particularly, this invention relates to a light-weight below-the-knee prosthesis having a foam keel portion such that a rubber foot may be readily adhered thereto.

BACKGROUND OF THE INVENTION

An artificial leg or prosthesis for a person who has a below-the-knee amputation and has tissues which are sensitive to the pressures and friction associated with the use of a prosthesis presents a significant problem if reasonably full use of the knee is to be preserved. As is the case with conventional prosthesis, these artificial limbs are usually fitted to the stump of the leg below the knee and strapped to the leg above the knee so that use of the knee for walking may be preserved. However, because this limb is fitted to the stump and the stump and limb are not one in the same, significant stresses during movement of the limb will tend to irritate the stump in the area where it contacts the prosthesis. Therefore, the need for a lightweight prosthesis is apparent particularly when fitting very weak geriatric patients with this type of prosthesis.

Numerous attempts have been made to develop a prosthesis which is both lightweight and structurally sound in order to perform functions similar to that of the natural limb. Some of these attempts have included an articulated toe and ankle section in an attempt to imitate nature by duplicating the functions of the natural foot. The importance of the cosmetic aspects of such an articulated limb are not to be denied, however, the simulation of these joints as well as that of the weight of a natural leg results in a limb which is difficult to maneuver due to an extreme excess of weight. The prosthesis is not a natural limb and, as mentioned above, cannot function in all respects as a natural integral limb.

In one attempt to overcome the shortcomings associated with the use of a below-the-knee prosthesis is set forth in U.S. Pat. No. 3,909,855 issued to Barredo. This below-the-knee prosthesis is a hollow rigid lightweight non-articulated prosthesis having a foreshortened foot which is fitted to the stump of a below-the-knee amputee. This prosthesis is of a unitary hollow shell formed of fiber glass and includes a foreshortened foot. This foreshortened foot portion is shortened by a length approximately equal to the toes of a natural foot and allows the prosthesis wearer to walk in a manner somewhat like that of a natural walk. However, the foreshortened foot exhibits no shock absorption characteristics and therefore any shock to the foot portion of this prosthesis will be absorbed completely by the stump of the wearer. Moreover, the foreshortened foot portion is not cosmetically pleasing to either the wearer or others.

A currently favored simplification of the articulated toe and ankle prosthesis is that of a prosthesis having a solid ankle portion and cushioned toe, heel and sole attached thereto, commonly known as the SACH foot design which is fixed to the bottom portion of the prosthesis.

In previously known SACH-type prosthesis, the socket portion of the prosthesis was formed in a conventional manner. The socket may then be adhered to a copolymer prosthesis having a solid ankle portion. Initially, the copolymer completely encompassed the solid ankle and consequently the cushioned or resilient heel was adhered directly to the bottom of the prosthesis, however, a reliable bond between the resilient heel and the copolymer prosthesis was not achievable due to the nature of the copolymer.

In order to overcome the above-mentioned problem, the bottom of the solid ankle portion was left exposed; i.e., with no copolymer material extending thereover and consequently a strong adhesion could be formed between the foam material of the solid ankle portion and the resilient material of the heel portion. However, because a majority of the foam is removed from within the prosthesis in order to significantly reduce the weight of the prosthesis, during use the keel would detach from the copolymer material of the prosthesis and pull out of the prosthesis resulting in a separation between the resilient heel and the shin portion of the prosthesis thus resulting in a lack of confidence in the structural integrity of the prosthesis. Additionally, because the prosthesis was susceptible to such structural damage, use of the prosthesis was limited to inactive below-the-knee amputees.

Clearly, there is a pressing need for a lightweight and structurally sound prosthesis that may be worn by both nonactive as well as active amputees who can wear the prosthesis while performing any activity without fear of any catastrophic failures.

SUMMARY OF THE INVENTION

A primary object of the present invention is to overcome the above-mentioned shortcomings associated with the previously known prostheses.

A particular object of the present invention is to provide a light weight prosthesis which may be worn by either an active or inactive below-the-knee amputee. This is achieved by removing substantially all of the foam material used to construct the support structure for molding a shin portion of the prosthesis thereon. This is carried out by grinding away from an interior of the shin member foam material wherein the foam material is accessed from both the proximal and distal ends of the prosthesis.

Another object of the present invention is to provide a prosthesis wherein the fear of catastrophic failure of the prosthesis is virtually eliminated. This is carried out by forming a retaining means in the keel portion of the prosthesis such that material forming the shin member will essentially lock the keel within the shin so as to prevent the keel from pulling out of the shin member during use.

A further object of the present invention is to reliably secure a resilient foot to the bottom surface of the keel. This is carried out by temporarily securing the foot to the bottom surface of the keel and forming channels about the periphery of the surface. These channels are then completely filled with an epoxy resin which reliably maintains the resilient foot in place.

These as well as other objects of the present invention are achieved by providing a prosthesis for fitting a below-the-knee stump including a socket for receiving the stump of a below-the-knee amputee, a keel having a peripheral groove formed about the periphery of a bottom surface thereof as well as a transverse groove extending from a lateral periphery of the keel to a medial periphery of the keel formed in the bottom surface. A tubular shin member extending from the socket means and surrounding the keel with a portion thereof extending into the retaining means while leaving a substantial portion of the bottom surface of the keel exposed and a resilient foot member secured to this exposed bottom surface.

The above-mentioned prosthesis is formed in accordance with the present invention by forming a socket conforming to the stump of the below-the-knee amputee, constructing a shin support including an ankle block and the keel in accordance with the size and stature of the amputee on the socket, machining a peripheral groove about the periphery of the bottom surface of the keel and a transverse groove extending from the lateral periphery to the medial periphery of the keel and the bottom surface thereof for retaining the keel in a predetermined position with respect to a shin member, and molding a sheet of copolymer material, preferably polytetrabutylene about the shin support, and into the retaining means and over the bottom surface of the keel to form the shin member. Next, all of the copolymer material is removed from the bottom surface of the keel except for that portion which has been molded into the grooves, a substantial portion of the material used to construct the shin support is removed from within the shin member and a resilient foot is secured to the exposed bottom surface of the keel. Also formed in both the lateral and medial sides of the keel are a plurality of bores for receiving a portion of the molded sheet of copolymer material to aid in maintaining the keel in the predetermined position with respect to the shin member.

The above, as well as other objects of the present invention, will become apparent from the drawings and detailed description set forth hereinbelow.

BRIEF DESCRIPTION OF THE DRAWINGS

FIG. 1 is a side elevational view of a prosthesis in accordance with the present invention with the stump portion of a below-the-knee amputee inserted therein.

FIG. 2 is a partially cross-section front elevational view of the prosthesis of FIG. 1.

DETAILED DESCRIPTION OF THE PREFERRED EMBODIMENT

Figure 3:
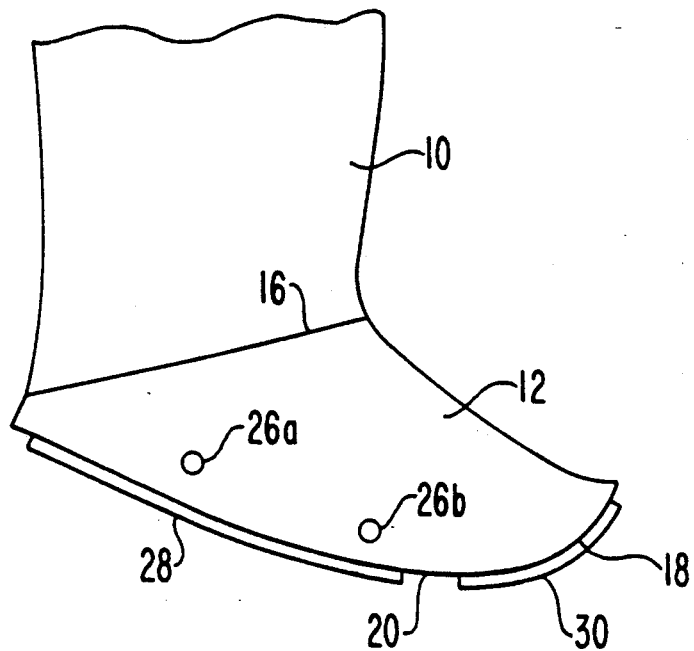
FIG. 3 is an elevational view of a keel and ankle block portion in accordance with the present invention.

Referring to the drawings and particularly to FIG. 1, a prosthesis 2 is illustrated having a socket 4 for receiving a stump 6 of a below-the-knee amputee. The prosthesis 2 of the present invention is formed of a ⅛" sheet of copolymer material, preferably polytetrabutylene which is heated in an oven and formed about a mold. This process will be described in greater detail hereinbelow. The prosthesis 2 includes the socket 4 for receiving the stump 6 and a shin portion 8 which extends downwardly from the socket and about an ankle block 10 and keel 12 which are best seen in FIG. 3. Attached to the bottom of the keel 12 is a resilient OTTO BOCK ™ No. 1S19 resilient heel, sole and toe section more commonly referred to as a foot 14. The foot 14 is adhesively secured to an exposed bottom portion of the keel 12 which will be described in greater detail hereinbelow.

As can be seen from FIG. 2, the upper portion of the shin 8 is fixed to the socket 4 in a conventional manner and extends downwardly therefrom and about the ankle block 10 and keel 12. The ankle block 10 and keel 12 are best illustrated in FIG. 3 wherein these members are illustrated as abutting one another at 17. During the manufacturing process of the prosthesis, a suitable ankle block 10 and keel 12 are selected in accordance with the size of the amputee to be fitted. The ankle block 10 is formed of OTTO BOCK ™ Pedelin Foam No. 617H12 and Hardener No. 617P21 as is the keel 12. As can be noted, the keel 12 takes the shape of the upper region of the foot and it is the lateral or outer side of the foot that is illustrated in FIG. 3. Once the appropriate sized ankle block 10 and keel 12 have been selected, these members are fixed relative to one another and the ankle block 10 is trimmed to achieve a smooth transition between the ankle block 10 and keel 12. These members are secured to one another in a conventional manner by way of an ankle bolt (not shown) inserted through the bolt hole 13 which is later removed when finishing the prosthesis.

Figure 4:
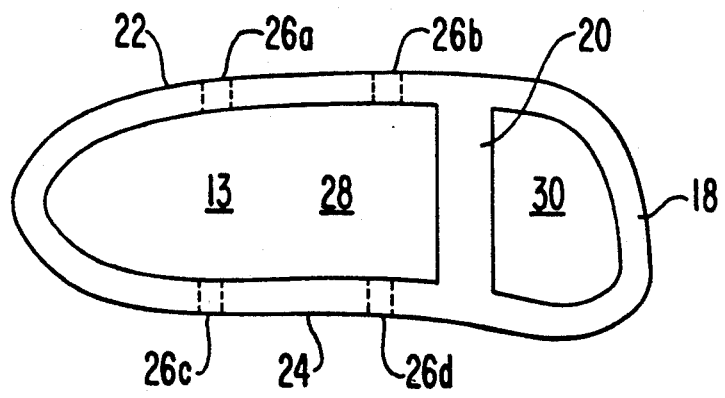
FIG. 4 is a bottom view of the keel illustrated in FIG. 3.

As can be noted from FIG. 3, and as is better illustrated in FIG. 4, a groove 18 is formed about the peripheral of the keel member with this groove being approximately ¼" wide and ⅛" deep. The groove 18 is in the form of a cut-out and extends about the entire periphery of the bottom of the keel 12. Also formed in the keel 12 is a transverse groove 20 which extends from the lateral side 22 to the medial side 24 of the keel. This groove is positioned approximately one inch posterior to the leading edge of the keel and is approximately ½" wide and ¼" deep. These grooves may be easily formed in the foam material of the keel by way of a hand-held grinder; however, in order to minimize manufacturing costs and time, these grooves may be either molded or machined into the keel during its original manufacture. Also formed in both the lateral side 22 and the medial side 24 of the keel 12 are bores 26a through 26d. These bores are approximately 5/16" wide and ¼" deep. While the preferred embodiment illustrates a pair of bores on each of the lateral and medial sides of the keel 12, any number of such bores may be provided so long as the structural integrity of the keel 12 is maintained. With the particular pattern of grooves set forth in the bottom portion of the keel 12, raised portions 28 and 30 are formed which contact the foot 14 when such foot is positioned adjacent thereto. While in the preferred embodiment, only one transverse groove 20 is illustrated, any number of grooves may again be present so long as the structural integrity of the keel 12 is maintained and a sufficient surface area is provided for contacting the foot 14. The significance of the above-mentioned grooves 18 and 20 as well as the bores 26a-26d and the raised surfaces 28 and 30 will become apparent from a discussion of the manufacturing process of the prosthesis set forth in greater detail hereinbelow.

As mentioned previously, the two major concerns of the prostheses is the effective weight and structural integrity of the prosthesis. By effective weight, it is meant the actual distribution of the weight in proportion to the overall weight. For example, the more weight which is distributed away from the socket 4 of the prosthesis, the greater the force required to maneuver such weight. Therefore, it is not only the overall weight of the prosthesis which is of concern, but effective weight thereof. The above-described 27 prosthesis achieves both of these criteria and is manufactured in the following manner.

Initially, a well-fitting positive mold of the residual limb of the below-the-knee amputee is formed in a conventional manner. Check sockets are often used to achieve this goal. The socket 4 is also manufactured in a conventional manner from a PELITE® liner of 3/16" firm PELITE® which is heated and molded over the cast in the conventional manner with a nylon sheath being pulled over the PELITE® liner and sprayed with silicone. Next, a ⅛" copolymer sheet, preferably of polytetrabutyline, is heated in an oven and subsequently draped over the cast which is positioned in a horizontal manner with the interior of the mold facing downward. This copolymer sheet is then seamed and vacuumed formed in a conventional manner to fabricate the socket. Excess plastic is trimmed about the cast with scissors with the remaining seam being flattened by rolling a dowel across the seam while applying a suitable amount of pressure. Care must be taken to assure that the area about the seam does not become excessively thin. The socket is then allowed to cool for approximately 30 minutes. After such time, a small hole is drilled in the distal end of the socket and an air gun is used to remove the socket and liner from the cast with a grinder being used to reduce the overall seam to approximately 1/16". It should be noted that by not stretching the copolymer material over the cast, once this material has set a minimal amount of shrinkage will be experience.

The thus-formed positive mold is then cleaned and all excess plastic is removed. The cast is then placed distal end up in a pipe jig and a 5-ply sock is then pulled over the cast. The plastic socket is then put back on the cast and a shin section is manufactured in the conventional manner using OTTO BOCH™ pedelin Foam No. 617H12 and a Hardener No. 617P21. By positioning the socket on the cast, this will prevent any distortions of the socket created by heat which is generated by the curing foam. Once this foam mixture has cured, the socket may then be removed from the cast.

An appropriate OTTO BOCH™ No. 1S19 foot with pedelin keel and ankle block is then selected in accordance with the size and stature of the amputee to be fitted with the prosthesis. The now-formed shin and socket section is then trimmed to an appropriate height and the ankle block is fitted to the distal end thereof in a conventional manner. Once this has been carried out, the thus-formed prosthesis is then positioned on the patient and any height or alignment changes can be made in the shin portion by cutting away portions of the foam and the subsequent re-attachment thereof. It should be noted that the foam material may be brittle and that care must be taken during this stage of the manufacturing process in order not to damage the foam structure.

Once the prosthesis is properly fitted to the patient, the prosthesis is shaped and smoothed and a solution of liquid plaster of Paris is sized over irregular areas of the limb. However, care must be taken so as to avoid the area 3 inches proximal to the ankle joint and any other areas where the cured plaster could not be readily removed as described below.

Once the prosthesis is properly shaped, the inside of the socket is coated with Vaseline® and filled with plaster and a vacuum pipe is inserted therein in a conventional manner and let stand to cure. The foot section 14 is then removed from the keel 12 and the bottom of the keel 12 is then machined in order to reach the configuration set forth in FIGS. 3 and 4 in accordance with a preferred embodiment of the invention.

With a small hand-held grinder, a groove approximately ¼" wide and ⅛" deep is machined about the entire peripheral edge of the bottom of the keel as illustrated in FIGS. 3 and 4. Subsequently, approximately 1" posterior of the leading edge of the keel 12, a transverse groove extending from the lateral side 22 of the keel 12 to the medial side 24 of the keel 12 approximately ½" in width and approximately ¼" deep is machined across the bottom of the keel 12. Again, the significance of such grooves will become apparent from the below description. Next, a pair of 5/16" diameter bores are drilled in both the lateral 22 and medial 24 sides of the keel 12 to a depth of approximately ¼". The first holes 26a and 26c on either side of the keel 12 are drilled approximately 1–2" anteriorly of the posterior of the keel 12 and the second holes 26b and 26d on either side of the keel 12 are positioned approximately 2" anterior of the respective first hole.

Once the desired configuration of the bottom portion of the keel is achieved, the vacuum pipe is again inserted into a pipe jig in order to maintain the prosthesis structure in a horizontal fashion with the anterior of the prosthesis facing upwardly. A knee-high stocking or other similar covering material is pulled over the prosthesis and tied off at the upper portion thereof. Any excess stocking accumulated at the bottom of the keel can be forced into the bolt hole 13. A sheet of ¼" copolymer material, preferably polytetrabutylene, is heated to a temperature which renders such material pliable, is then positioned adjacent the prosthesis structure and subsequently vacuumed-formed thereover in a conventional manner. A seam is formed on the bottom of the keel and along the posterior section of the prosthesis. This seam is then trimmed to within ¼" and subsequently gently rolled with a dowel to form a smooth and inconspicuous seam. This material is then allowed to cool for approximately 12 hours before the excess plastic is removed. Once the material has cooled, all plastic which overlies the raised portions 28 and 30 of the keel is removed while the material within the grooves 18 and 20 remains. Further, plastic material will subside into the bores 26a–26d. It can be noted that upon the conclusion of the manufacturing process, the plastic material which has been maintained within the grooves 18 and 20 will securely retain the keel 12 portion within the now copolymer coated prosthesis.

The prosthesis is now in its final stages wherein the plaster is removed from within the socket and a 1" spade drill bit is used to drill up into the prosthesis from the bolt hole 13 in order to remove as much of the foam material from within the copolymer shell as possible. The drilling is continued upward through the distal end of the socket with care being taken so as to not contact the copolymer coating. All of the foam material is then removed from a point approximately 2" above the ankle joint seam 17 to the distal end of the socket. The already formed hole 16 in the socket may be enlarged in order to facilitate removal of the foam material. A router with a 40 grit cone can be used for quick and easy removal of the foam material. Again, care must be taken in order not to excessively contact the interior of the copolymer shell of the prosthesis.

It should also be noted that all foam material which can be removed without jeopardizing the structural integrity of the prosthesis must be removed in order to achieve as light a prosthesis as possible.

The exposed surfaces of the raised portions 28 and 30 are then sanded in order to form a highly advantageous surface for adhering the foot 14 to the bottom of the prosthesis. A plug having a diameter of approximately 1" and a depth of approximately 5/16" and formed of PELITE ® foam material is snugly forced into the keel hole in order to seal off this opening. In a similar manner, a plug is placed in the bolt hole of the foot in order to provide a smooth and congruent bottom surface thereof.

The foot 14 is then positioned on the keel section and temporarily secured in place by masking tape or other suitable material. A channel is thus formed between the foot 14 and the keel 12 which readily receives adhesive material therein. The masking tape is wrapped sufficiently around the foot 14 in order to provide only one small access opening to the channels in the heel region of the foot 14 which are formed by the grooves 18 and 20, the foot 14 and the masking tape. This will allow the adhesive material to flow throughout the bonding surfaces between the foot 14 and the keel 12. In accordance with the preferred embodiment, a mix of R200 epoxy resin and hardener are used for this purpose. With the prosthesis positioned such that the toe is pointed in a downward direction, the adhesive is poured into the access hole left adjacent the heel of the foot 14. The adhesive material will settle throughout the channels, therefore, the adhesive must be periodically refilled. Once this is completed the prosthesis in its present stage must be allowed to dry for at least 24 hours. Once completed, any excess resin is removed and all of the surfaces of the prosthesis are smoothed by using a fine grit sandpaper resulting in a smooth and congruent prosthesis. The foot portion 14 may then be painted any suitable color for cosmetic purposes. Further, cosmetic stockings can then be put on the prosthesis for cosmetic improvement.

By manufacturing the prosthesis in accordance with the above-described process, the overall weight of the prosthesis can be reduced from 3½ lbs. to 1½-2 lbs. without sacrificing any structural integrity. Moreover, the user can be confident that the catastrophic failures associated with previous prosthetic devices will not occur regardless of whether the user is active or inactive.

While the invention has been described with reference to a preferred embodiment, it should be appreciated by those skilled in the art that the invention may be practiced otherwise and as specifically described herein without departing from the spirit and scope of the invention. It is, therefore, to be understood that the spirit and scope of the invention be limited only by the appended claims.

What is claimed is:

1. A method of manufacturing a prosthesis for a below-the-knee amputee comprising the steps of:
   forming a socket for receiving a stump of the below-the-knee amputee;
   constructing a shin support about said socket including an ankle block and keel in accordance with the size and stature of the amputee about said socket;
   forming a retaining means in a bottom surface of said keel for retaining said keel in a predetermined position with respect to said socket;
   molding a sheet of copolymer material about said shin support, into said retaining means and over said bottom surface of said keel to form a shin member;
   removing the copolymer material from said bottom surface of said keel except for that portion which has been molded into said retaining means;
   removing a substantial portion of material used to construct said shin support from within said shin member; and
   securing a foot member to said keel.

2. The method as defined in claim 1, wherein said shin support is formed of a foam material.

3. The method as defined in claim 1, wherein said step of forming said retaining means includes machining a peripheral groove about the periphery of said bottom surface of said keel.

4. The method as defined in claim 3, wherein said step of forming said retaining means further includes machining a transverse groove in said bottom surface of said keel extending from a lateral periphery of said keel to a medial periphery of said keel.

5. The method as defined in claim 3, wherein said step of forming said retaining means further includes drilling at least one bore in each of a medial and lateral sides of said keel.

6. The method as defined in claim 3, wherein said peripheral groove is approximately ¼ inch in width and approximately ⅛ inch in depth.

7. The method as defined in claim 3, wherein said transverse groove is formed approximately 1 inch posterior of a leading edge of said keel.

8. The method as defined in claim 3, wherein said transverse groove is approximately ½ inch in width and approximately ⅛ inch in depth.

9. The method as defined in claim 1, wherein the step of securing said foot includes the steps of temporarily adhering said foot to said keel thereby forming channels about a securing surface of said foot and filling said channels with epoxy resin to permanently secure said foot to said keel.

* * * * *